United States Patent
Eberting

(10) Patent No.: US 10,918,652 B2
(45) Date of Patent: Feb. 16, 2021

(54) COMPOSITIONS FOR THE TREATMENT OF DERMATOLOGICAL DISEASES AND DISORDERS

(71) Applicant: CLARIDEI LABORATORIES, INC., Alpine, UT (US)

(72) Inventor: Cheryl Lee Eberting, Alpine, UT (US)

(73) Assignee: Claridei Laboratories, Inc., Alpine, UT (US)

( * ) Notice: Subject to any disclaimer, the term of this patent is extended or adjusted under 35 U.S.C. 154(b) by 0 days.

(21) Appl. No.: 16/509,356

(22) Filed: Jul. 11, 2019

(65) Prior Publication Data
US 2019/0336517 A1  Nov. 7, 2019

Related U.S. Application Data

(63) Continuation of application No. 15/127,670, filed as application No. PCT/US2015/021870 on Mar. 20, 2015, now abandoned.

(60) Provisional application No. 61/971,416, filed on Mar. 27, 2014, provisional application No. 61/968,073, filed on Mar. 20, 2014.

(51) Int. Cl.

| | | |
|---|---|---|
| A61K 31/7004 | (2006.01) | |
| A61K 31/198 | (2006.01) | |
| A61K 36/73 | (2006.01) | |
| A61K 9/00 | (2006.01) | |
| A61K 31/19 | (2006.01) | |
| A61K 47/12 | (2006.01) | |
| A61K 31/366 | (2006.01) | |
| A61K 47/18 | (2017.01) | |
| A61K 47/32 | (2006.01) | |
| A61K 47/36 | (2006.01) | |
| A61K 31/194 | (2006.01) | |
| A61K 47/10 | (2017.01) | |

(52) U.S. Cl.
CPC ........ *A61K 31/7004* (2013.01); *A61K 9/0014* (2013.01); *A61K 31/19* (2013.01); *A61K 31/194* (2013.01); *A61K 31/198* (2013.01); *A61K 31/366* (2013.01); *A61K 36/73* (2013.01); *A61K 47/10* (2013.01); *A61K 47/12* (2013.01); *A61K 47/183* (2013.01); *A61K 47/32* (2013.01); *A61K 47/36* (2013.01)

(58) Field of Classification Search
CPC .... A61K 9/0014; A61K 31/19; A61K 31/366; A61K 47/12; A61K 47/183
See application file for complete search history.

(56) References Cited

U.S. PATENT DOCUMENTS

| | | | | |
|---|---|---|---|---|
| 7,622,434 | B2 * | 11/2009 | Rogozinski | A01N 59/00 424/665 |
| 2004/0091558 | A1 * | 5/2004 | Lutz | A01N 35/02 424/745 |
| 2007/0265352 | A1 * | 11/2007 | Roeding | A01N 31/02 514/738 |

FOREIGN PATENT DOCUMENTS

| | | | | |
|---|---|---|---|---|
| KR | 100760698 B1 * | 10/2007 | | A61K 8/463 |
| KR | 100879093 B1 * | 1/2009 | | |
| WO | WO-2009014327 A2 * | 1/2009 | | A61K 8/345 |

OTHER PUBLICATIONS

Ash et al., Handbook of Cosmetic and Personal Care Additives, 2nd ed., vol. 1-2, 2013.*

* cited by examiner

*Primary Examiner* — Gina C Justice

(74) *Attorney, Agent, or Firm* — Phillips Winchester; Justin K. Flanagan

(57) ABSTRACT

The present disclosure is directed to topical dermatological formulations, dermatological cleansing compositions, and bathwater conditioners designed to acidify the skin, and their use for restoring epidermal acidity, restoring a the epidermal barrier, inhibiting inflammation, establishing an environment appropriate for maintaining a balanced symbiotic microbiome, and inhibiting the growth of pathogenic microorganisms in the epidermis—the outer layer of mammalian skin.

8 Claims, No Drawings

COMPOSITIONS FOR THE TREATMENT OF DERMATOLOGICAL DISEASES AND DISORDERS

RELATED APPLICATIONS

This application is a continuation of the U.S. National Stage application Ser. No. 15/127,670, filed Sep. 20, 2016, which claims benefit of International Application No. PCT/US2015/021870, filed on Mar. 20, 2015, which claims the benefit of U.S. Provisional Application Ser. No. 61/968,073, filed Mar. 20, 2014, and U.S. Provisional Application Ser. No. 61/971,416, filed Mar. 27, 2014. All of these applications are incorporated by reference in their entirety.

TECHNICAL FIELD

The present disclosure is directed to topical dermatological formulations, dermatological cleansers, and bathwater conditioners, and to their use for restoring an epidermal acid mantle and/or repairing or restoring a disrupted epidermal barrier. By restoring the epidermal acid mantle, the disclosed compositions can inhibit inflammation, promote the growth of a balanced symbiotic epidermal microbiome, inhibit the growth of pathogenic microorganisms, positively alter the synthesis and processing of lipids in underlying layers of the skin, beneficially affect desquamation, and treat a variety of dermatological diseases and disorders that share a hallmark of an inordinately high epidermal pH.

BACKGROUND

Human skin is normally acidic, ranging in pH values from about 4 to about 6. This phenomenon was recognized as early 1892 by Heuss, and was further described in 1928 by Schade and Marchionini, who coined the German term, Säuremantel (Der Säuremantel der Haut nach Gaskettenmessngen. *Klin. Wochenschr.* 1928, 7:12-14) to describe the protective "acid mantle" formed by healthy, and normally acidic, skin. The permeability barrier presented by healthy skin arises from the stratum corneum, which exhibits a hydrophobic character resulting from the distribution and organization of its lipid contents, which are arranged in a series of lamellar bilayers (Elias and Menon; Structural and lipid biochemical correlates of the epidermal permeability barrier. *Adv. Lipid Res.,* 1991; 24:1-26). Although still an area of active investigation, it appears that the low pH of normal human skin can be ascribed to several endogenous mechanisms, including the activity of the sodium/proton pump protein, NHE1, and free fatty acid conversion from phospholipids by members of the secretory phospholipase $A_2$ ($sPLA_2$) family of enzymes. (Chan and Mauro. Acidification in the epidermis and the role of secretory phospholipases. *Dermato-Endocrinology* April/May/June 2011, 3:84-90.) Moreover, the epidermal barrier specifically resides in the extracellular lipid membranes of the stratum corneum, and an acidic pH is necessary to maintain the competency of the barrier against various insults. An important part of that barrier includes, for example, free fatty acids in the extracellular space of the stratum corneum, that, when partially ionized at pH values of 4.5 through 6.0, form protective lamellar liquid crystals.

Over the last 10 years or so, it has been demonstrated that epidermal barrier homeostasis is strongly influenced by skin pH, and that the appropriate acidity of skin is important for maintaining stratum corneum integrity and cohesion, promoting normal skin shedding (desequamation), and defending against colonization by pathogenic microorganisms. See Ali and Yosipovitch (Skin pH: From Basic Science to Basic Skin Care, *Acta Derm Veneroel,* 2013, 93:261-267) for a recent review. Indeed, the formation and maintenance of the normal epidermal barrier requires the stepwise generation, liberation and processing of lipophilic components by several classes of enzymes in an acidic milieu. Among the classes of enzymes involved in the processing of lipophilic components are two families, the β-glucocerebrosidases and acidic sphingomyelinases, which have pH optima of 5.6 and 4.5, respectively (Rippke, et al., The acidic milieu of the horny layer: New findings on the physiology and pathophysiology of skin pH. *Am. J. Clin. Dermatol.* 2002, 3:261-272). These two families of enzymes are involved in the synthesis of ceramides, which are known to be critical components of the normal permeability barrier of healthy skin. In view of the acidic pH optima of these two families of enzymes, and their central role in ceramide production, it is perhaps not surprising that processing of lipids secreted by lamellar bodies, and the formation of lamellar structures, requires an acidic environment (Mauro, et al. Barrier recovery is impeded at neutral pH, independent of ionic effects: Implications for extra-cellular lipid processing. *Arch. Dermatol. Res.* 1998, 290:215-222). If the pH of that normally-acidic environment rises, lipid processing is disrupted, and the epidermal barrier can, in turn, be disturbed or disrupted.

Although the acidic pH of healthy stratum corneum is particularly important for epidermal barrier homeostasis and also for the integrity and cohesion of the stratum corneum layer a decreasing gradient of free hydrogen ions ($H^+$) apparently occurs as corneocytes make their way to the surface of the skin. Also, this reverse gradient appears to be important for normal desquamation. Indeed, it is believed that the pH of skin increases slightly (to more neutral values) as the dead corneocytes migrate towards the surface of the skin. Not surprisingly, and unlike the enzymes involved in ceramide synthesis and epidermal barrier establishment, the enzymes involved in the desquamation process appear to have neutral pH optima. These enzymes include serine proteases, kallikrein 5 (stratum corneum tryptic enzyme) and kallikrein 7 (stratum corneum chymotryptic enzyme), which facilitate desquamation through the degradation of desmoglein 1. It has therefore been postulated that elevation of local pH towards the surface of the stratum corneum leads to the activation of these serine proteases, and the corresponding deactivation of the enzymes responsible for ceramide synthesis. As serine protease activity increases, lamellar body secretion is blocked, and the corneocytes are readied for desquamation.

The epidermal permeability barrier characteristic of healthy skin imparts the skin with an innate resistance to external insults while protecting the underlying tissues from dehydration. The "acid mantle" of healthy skin promotes the growth of the normal microbiota that constitutes the microbiome of healthy skin. The normal bacterial and fungal flora that constitute the microbiome of healthy skin show a preference for the weakly acidic conditions found on and in healthy skin.

In addition to promoting the growth of a healthy microbiome as a means of defending against colonization by pathogens, the human body has evolved several other lines of defense against pathogenic microbial invasion. For example, human sweat contains a natural antimicrobial peptide, named dermicidin. Dermicidin shows antimicrobial activity against a variety of pathogenic microorganisms. Dermicidin is known to be a more effective bacteriocide at pH 5.5 than at pH 6.5. (Schittek, et al., Dermicidin: A novel human antibiotic peptide secreted by the sweat glands. *Nat. Immumol.* 2001, 2:1133-1137.)

Sweat also contains nitrates, which are converted to nitrites by resident bacteria. The resulting nitrites are known to form reactive nitrogen species in an acidic milieu, which further defend against colonization by bacterial pathogens. (Weller, et al., Antimicrobial effect of acidified nitrite on dermatophyte fungi, *Candida* and bacterial skin pathogens. *J. Appl. Microbiol.* 2001, 90:648-652).

In view of the above, it should not come as a surprise that when the acid mantle is compromised, there appear to be wide-ranging changes in the skin that negatively affect the epidermal permeability barrier. Moreover, several dermatoses known to involve a disruption in the permeability barrier have also been found to be associated with alterations in pH consistent with a disruption in the normal acid mantle. Consequently, there is a clear need for topical dermatological formulations, dermatological cleansers, and bath water conditioners that can be used to reestablish and/or maintain the normal acid mantle characteristic of normal, healthy skin.

Additionally, healthy skin exhibits a characteristic and complex transdermal calcium ($Ca^{2+}$) gradient from the base to the surface of the epidermis. Specifically, healthy mammalian epidermis displays low levels of $Ca^{2+}$ in the basal epidermal layers (i.e., in the stratum basale), progressively increasing levels through the overlying stratum *spinosum*, reaching a peak towards the outer stratum *granulosum*, and declining through the stratum lucidium and stratum corneum. This characteristic complex gradient is thought to be important for permeability barrier homeostasis and epidermal cell differentiation. Evidence for the importance of this characteristic gradient comes in the form of studies in which there is acute barrier disruption caused by organic solvents, detergents or tape-stripping of the stratum corneum. After all these insults, the $Ca^{2+}$ gradient reappears after 6 hr, during which time the permeability barrier is restored in parallel. (Elias, et al., Origin of the epidermal calcium gradient: Regulation by barrier status and role of active vs passive mechanisms. *J. Invest. Dermatol.* 2002, 119:1269-1274.)

Consequently, there is a clear need for topical dermatological formulations, dermatological cleansers, and bath water conditioners that can be used to reestablish and/or maintain the calcium gradient that is characteristically found in normal, healthy skin, and promote the establishment of an intact, resilient permeability barrier.

DETAILED DESCRIPTION

The present disclosure provides topical dermatological formulations, dermatological cleansers, and bath water conditioners that can be used to repair or restore the epidermal acid mantle and thereby promote the repair and restoration of a disrupted epidermal barrier. The present disclosure also provides topical dermatological formulations, dermatological cleansers, and bath water conditioners that can be used to maintain the epidermal acid mantle and thereby maintain a robust and healthy epidermal barrier. The present disclosure also provides topical dermatological formulations, dermatological cleansers, and bath water conditioners that can be used to restore a transepidermal calcium gradient reminiscent of that observed in healthy skin.

By restoring and maintaining the epidermal acid mantle, the disclosed topical dermatological formulations, dermatological cleansers, and bath water conditioners can inhibit dermal/epidermal inflammation, promote the growth of a balanced symbiotic epidermal microbiome, inhibit the growth of pathogenic microorganisms, positively alter the synthesis and processing of lipids in underlying layers of the skin, beneficially affect desquamation, and effectively treat a variety of dermatological diseases and disorders characterized in part by an inordinately high (i.e., neutral or alkaline) pH of the affected skin.

By restoring and maintaining a transepidermal calcium gradient reminiscent of that observed in healthy skin, the disclosed topical dermatological formulations, dermatological cleansers, and bath water conditioners can promote the normal differentiation of cells as observed in healthy skin from the stratum basale at the basement membrane, to the surface of the stratum corneum. Moreover, by restoring and maintaining a transepidermal calcium gradient reminiscent of that observed in healthy skin, the disclosed topical dermatological formulations, dermatological cleansers, and bath water conditioners can promote the repair and restoration of an effective permeability barrier, which is required for skin health.

Acidifying Agents

The topical dermatological formulations, dermatological cleansers, and bath water conditioners of the present disclosure contain acidifying agents that are carefully chosen to be compatible with the skin, since the topical dermatological formulations, dermatological cleansers, and bath water conditioners will be in direct contact with the skin. Moreover, the concentration of acidifying agents is carefully selected to provide an amount of free hydrogen ions ($H^+$) sufficient to achieve the desired amount of epidermal acidification. Generally, the acidifying agents used in the topical dermatological formulations, dermatological cleansers, and bath water conditioners of the present disclosure are weak organic acids that partially dissociate in aqueous solutions.

The topical dermatological formulations, dermatological cleansers, and bath water conditioners of the present disclosure therefore comprise a weak organic acid, or combination of weak organic acids, as acidifying agents sufficient to impart the formulation with the desired acidic pH, which ranges from about pH 4.0 to about pH 6.0. In some embodiments, the weak organic acids are sufficient to impart the formulation with a pH ranging from about 4.2 to about 6.0. In other embodiments, the weak organic acids are sufficient to impart the formulation with a pH ranging from about 4.3 to about 5.9. In other embodiments, the weak organic acids are sufficient to impart the formulation with a pH ranging from about 4.4 to about 5.8. In other embodiments, the weak organic acids are sufficient to impart the formulation with a pH ranging from about 4.5 to about 5.7. In other embodiments, the weak organic acids are sufficient to impart the formulation with a pH ranging from about 4.6 to about 5.6. In other embodiments, the weak organic acids are sufficient to impart the formulation with a pH ranging from about 4.7 to about 5.5. In other embodiments, the weak organic acids are sufficient to impart the formulation with a pH ranging from about 4.8 to about 5.4. In other embodiments, the weak organic acids are sufficient to impart the formulation with a pH ranging from about 4.9 to about 5.3. In other embodiments, the weak organic acids are sufficient to impart the formulation with a pH ranging from about 5.0 to about 5.2. In other embodiments, the weak organic acids are sufficient to impart the formulation with a pH of about 4.6, about 4.8, about 5.0, about 5.2, about 5.4, or about 5.6.

For the topical dermatological formulations and cleansers of the present disclosure, the weak acid can be present in concentrations ranging from about 0.002 wt % to about 5 wt %. In some embodiments of the topical dermatological formulations and cleansers of the present disclosure, the weak acid can be present in concentrations ranging from about 0.005 wt % to about 1 wt %. In some embodiments of the topical dermatological formulations and cleansers of the present disclosure, the weak acid can be present in concentrations ranging from about 0.1 wt % to about 0.8 wt %. In some embodiments of the topical dermatological formulations and cleansers of the present disclosure, the weak acid can be present in concentrations ranging from about 0.2 wt % to about 0.75 wt %.

In some embodiments, the weak organic acids used in the topical dermatological formulations, dermatological cleansers, and bath water conditioners of the present disclosure are small (i.e., $C_1$-$C_6$) monocarboxylic acids, such as formic acid, acetic acid, propionic acid, butyric acid, valeric acid, or caproic acid. These small monocarboxylic acids are also known as methanoic acid, ethanoic acid, propanoic acid, butanoic acid, pentanoic acid, and hexanoic acid, respectively. These small (i.e., $C_1$-$C_6$) monocarboxylic acids have the advantage of being relatively soluble in aqueous solutions.

In some embodiments, the weak organic acids used in the topical dermatological formulations, dermatological cleansers, and bath water conditioners of the present disclosure are small (i.e., $C_2$-$C_9$) dicarboxylic acids, such as oxalic acid, malonic acid, succinic acid, glutaric acid, adipic acid, pimelic acid, suberic acid or azelaic acid. These small dicarboxylic acids are also known as ethanedioic acid, propanedioic acid, butanedioic acid, pentanedioic acid, hexanedioic acid, heptanedioic acid, octanedioic acid and nonanedioic acid, respectfully. These small (i.e., $C_2$-$C_9$) dicarboxylic acids have the advantage of being relatively soluble in aqueous solutions and having two carboxylic groups per molecule. In some embodiments, these small i.e., $C_2$-$C_9$) dicarboxylic acids include unsaturated dicarboxylic acids, such as maleic acid or fumaric acid, which is otherwise known as trans-butenedioic acid.

In some embodiments, the weak organic acids used in the topical dermatological formulations, dermatological cleansers, and bath water conditioners of the present disclosure are small (i.e., $C_6$-$C_9$) tricarboxylic acids, such as citric acid, isocitric acid, cis- and trans-aconitic acid, propane-1,2,3-tricarboxylic acid (also known as tricarballylic acid or carballylic acid), and trimesic acid (also known as benzene-1,3,5-tricarboxylic acid). These small (i.e., $C_6$-$C_9$) tricarboxylic acids have the advantage of being relatively soluble in aqueous solutions and having three carboxylic groups per molecule.

In some embodiments, the weak organic acids used in the topical dermatological formulations, dermatological cleansers, and bath water conditioners of the present disclosure are small (i.e., $C_4$-$C_8$) hydroxy acids, such as the alpha hydroxy acids, glycolic acid, malic acid, lactic acid (also known as hydroxypropanoic acid), isocitric acid, tartaric acid, mandelic acid (phenyl glycolic acid), and benzilic acid (diphenyl glycolic acid).

In some embodiments, the weak organic acids used in the topical dermatological formulations, dermatological cleansers, and bath water conditioners of the present disclosure are small (i.e., $C_6$-$C_8$) polyhydroxy acids, and their lactones, which in many cases can also be referred to as sugar acids. For example, in some embodiments, the weak organic acids used in the topical dermatological formulations, dermatological cleansers, and bath water conditioners can be gluconic acid and/or its lactone, glucono delta-lactone, which is also known as gluconolactone, as further described below.

"Glucono delta-lactone," which is also known as "gluconolactone," "D-Glucono-1,5-lactone," "1,5-D-glucono-lactone," "1,5-delta-glucono lactone," "D-Gluconic acid δ-lactone," or "GDL," refers to a lactone (cyclic ester) or oxidized derivative of D-Gluconic acid, with the following structure:

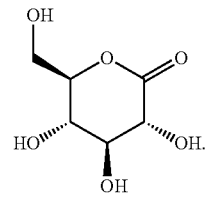

Gluconolactone is a polyhydroxy acid (PHA) that is capable of chelating metals and may also scavenge free radicals. When dissolved in water, it is partially hydrolyzed to gluconic acid, with the balance between the lactone form and the acid form established as a chemical equilibrium. Gluconic acid is a noncorrosive, nonvolatile, nontoxic, mild organic acid with a pKa of 3.7 (Ramachandran et al. Gluconic Acid: A Review. Food Technol. Biotechnol. 2006; 44(2): 185-95.). On account of these properties, glucono delta-lactone is used as both a "sequestrant" and an "acidifier" in foods. "Sequestrants," a term generally used in the context of food additives, improve the quality and stability of the food products by forming chelate complexes with metal ions, especially copper, iron and nickel ions, which otherwise serve as catalysts in the oxidation of the fats in the food. In particular, by chelating free iron ions, glucono delta-lactone blocks the formation of hydroxyl radicals, thereby serving as an antioxidant.

In addition, glucono delta-lactone is also known to have photoprotective activity (Bernstein, et al., The polyhydroxy acid gluconolactone protects against ultraviolet radiation in an in vitro model of cutaneous photoaging. Dermatol. Surg. 2004 February, 30(2 Pt 1):189-95.) and, as an alpha hydroxyacid, glucono delta-lactone, is known to enhance stratum corneum desquamation, improve skin appearance, and prevent skin irritation (Berardesca et al., Alpha hydroxyacids modulate stratum corneum barrier function. Br. J. Dermatol. 1997 December, 137(6):934-8). Consequently, glucono delta-lactone is utilized as an acidifying agent in some embodiments of the disclosed formulations for its ability to acidify the skin, protect the skin from damage by ultraviolet radiation, lessen or prevent irritation, enhance desired stratum corneum desquamation, and improve skin appearance. In some embodiments, glucono delta-lactone is used in combination with other weak organic acids, as described herein.

In some embodiments, the weak organic acids used in the topical dermatological formulations, dermatological cleansers, and bath water conditioners of the present disclosure are so-called "sugar acids," which are monosaccharides having a carboxyl group attached, and which in many cases can be referred to as polyhydroxyacids. For example, in some embodiments, the weak organic acids used in the dermatological formulations can be glyceric acid, xylonic acid, ascorbic acid, aldonic acid, ulosonic acid, uronic acid, glucuronic acid, galacturonic acid, iduronic acid, mucic acid, saccharic acid, or aldaric acid.

In some embodiments, the weak organic acids used in the topical dermatological formulations, dermatological cleansers, and bath water conditioners of the present disclosure are so-called bionic acids, which have a carbohydrate monomer linked to a polyhydroxy acid. For example, in some embodiments, the weak organic acids used in the dermatological formulations are lactobionic acid (a disaccharide formed by the condensation of gluconic acid and galactose), maltobionic acid, and cellobionic acid, or combinations thereof.

In some embodiments, the weak organic acids used in the topical dermatological formulations, dermatological cleansers, and bath water conditioners of the present disclosure are provided as an intrinsic component of a natural product. For example, in some embodiments the weak organic acid is acetic acid, which is provided as a component of vinegar. In some embodiments the natural product containing the acidifying agent has been processed, for example, by spray drying, to provide the natural product containing the weak organic acid in a form that is altered from the original. For example, in some embodiments the weak organic acid is acetic acid, which is provided as a component of powdered vinegar. In these embodiments in which the weak organic acid is provided as a component of a natural product, such as vinegar, or a processed natural product, such as vinegar powder, the natural product, or processed natural product can provide a variety of other components. For example, among the other components that may be provided along with the acetic acid of vinegar are, gallic acid, 4-hydroxybenzaldehyde, catechin, vanillic acid, caffeic acid, syringic acid, vanillin, syringaldehyde, p-coumaric acid, m-coumaric acid, anisaldehyde, epicatechin, sinapic acid, salicylaldehyde, scopoletin, veratraldehyde and o-coumaric acid. (Gálvez et al., Analysis of polyphenolic compounds of different vinegar samples. *Zeitschrift für Lebensmittel-Untersuchung and Forschung;* 1994, 199(1):29-31 and Cerezo, et al. The phenolic composition of red wine vinegar produced in barrels made from different woods. *Food Chem.* 2008, 109(1):606-615.) Generally these other components are found in very low amounts, or even trace amounts, which are barely detectable.

In some embodiments, the acidifying agent used in the topical dermatological formulations, dermatological cleansers, and bath water conditioners is a single species of weak organic acid selected from those species disclosed above. In other embodiments the acidifying agent used in the dermatological formulations and bathwater conditioners is a carefully chosen combination of different weak organic acid species selected from those species disclosed above.

Calcium Chelation Agent

The topical dermatological formulations, dermatological cleansers, and bath water conditioners of the present disclosure can also comprise a component, or components, that chelate calcium. In some embodiments, the calcium chelator is ethylenediaminetetraacetic acid, or EDTA. In other embodiments, the calcium chelator is ethylene glycol tetraacetic acid, or EGTA. In still other embodiments, the calcium chelator is combination of EDTA and EGTA.

When the calcium chelator used in the topical dermatological formulations or dermatological cleansers is EDTA, it can be found in concentrations of around 0.05 wt %. In some embodiments EDTA is used as the calcium chelator, and the EDTA is present in a concentration ranging from about 0.001 wt % to about 0.5 wt %. In some embodiments EDTA is used as the calcium chelator, and the EDTA is present in a concentration ranging from about 0.01 wt % to about 0.25 wt %. In some embodiments EDTA is used as the calcium chelator, and the EDTA is present in a concentration ranging from about 0.02 wt % to about 0.1 wt %. In some embodiments EDTA is used as the calcium chelator, and the EDTA is present in a concentration ranging from about 0.04 wt % to about 0.08 wt %.

While not wishing to be bound by any particular theory, the amount and type of calcium chelator is carefully chosen to provide sufficient chelation ability to remove calcium from the outermost layers of the stratum corneum, and to encourage the formation of a calcium gradient reminiscent of that of healthy skin, in which calcium concentrations gradually increase through the stratum basale and the stratum *spinosum*, to reach a peak in the outer stratum *granulosum*, before diminishing through the stratum lucidum and stratum corneum.

Thickening Agents, Viscosity Enhancing Agents, and/or Gelling Agents

In some embodiments, the topical dermatological formulations and dermatological cleansers of the present disclosure comprise a thickening agent, viscosity enhancing agent, or gelling agent, or a combination thereof. These agents all act to increase the viscosity of the formulation, and can also impart other desirable characteristics to the dermatological formulations such as gelation or thixotrophic behavior. The thickening agent, viscosity enhancing agent, or gelling agent, can be selected from any such agents know to be compatible with, and non-harmful to, human skin.

In some embodiments, the dermatological compositions of the present disclosure are water soluble gels that, once applied, provide sustained local concentrations of the acidifying and/or calcium chelating agents of the formulation. Such gel formulations, can for example utilize a hydrophilic gelling agent, which may be selected from the general classes of carboxyvinyl polymers, natural gums, and clays. Lipophilic gelling agents which may be used include modified clays such as bentones, metal salts of fatty acids, such as aluminum stearates, and hydrophobic silica.

In some embodiments the gelling agent employed in the topical dermatological formulations of dermatological cleansers of the disclosure is a naturally occurring gelling agent such as a natural gum composed of polysaccharides. In some embodiments the gelling agent employed in the dermatological formulations of the disclosure is selected from xanthan gum, gellan gum, guar gum, locust bean gum, gum arabic, agar, alginic acid, sodium alginate, potassium alginate, ammonium alginate, carrageenan, tragacanth, pectin and gelatin. In some embodiments the gelling agent employed in the dermatological formulations of the disclosure is a synthetically processed polysaccharide gelling agent, such as methylcellulose, carboxymethylcellulose, ethylcellulose, hydroxyethylcellulose, hydroxyproyl cellulose. In some embodiments the gelling agent employed in the dermatological formulations of the disclosure is a synthetically produced gelling agent, such as carbomers, poloxamers, or polyvinyl alcohols. In some embodiments the gelling agent employed in the dermatological formulations of the present disclosure is a particular type of carbomer, such as the carbomer comprising a cross-linked homopolymer of acrylic acid, such as a Carbopol®. In particular dermatological formulations of the present disclosure, the gelling agent can be Carbopol® Ultrez 30 polymer, Carbopol® 910, Carbopol® 934, Carbopol® 934P, Carbopol® 940 or Carbopol® 941, or combinations thereof, which are manufactured and marketed Lubrizol Advanced Materials, Inc., Cleveland, Ohio.

In some embodiments the gelling agent employed results in the formation of stable hydrogels that exhibit thixotropic properties. In these embodiments, the gelling agent can be chosen from natural clay and synthetic clay. In come embodiments, the hydrogel can be achieved by the use of an entirely synthetic mineral which is akin to the natural clay mineral hectorite in structure and composition. Unlike natural clay, however, a synthetic mineral is typically free of impurities yet can be equal in structure to natural hectorite. One such synthetic mineral is listed in the American Chemical Society's Chemical Abstracts Service (CAS) under the name sodium lithium magnesium silicate (Registration No. 53320-86-8) and in the Cosmetic, Toiletries and Fragrance Association (CTFA) dictionary as sodium magnesium silicate. This synthetic mineral is sold commercially under the trade name LAPONITE®, a registered trademark of Southern Clay Products, Inc., Gonzales, Tex. Other non-limiting examples of the at least one gelling agent include magnesium aluminum silicates, smectite clays, and an amorphous clay mineral, such as allophone; two-layer type crystalline clay minerals, such as equidimensional crystal, kaolinite, and nacarite; elongate crystals, such as halloysites; three-layer type crystalline clay minerals, such as sodium montmorillonite, calcium montmorillonite, sauconite, vermiculite, nontronite, saponite, hectorite, and bentonite; chain structure crystalline clay minerals, such as attapulgite, sepiolite, and palygorskite; and mixtures thereof.

Without being limited to any particular theory, it is believed that the swelling properties of the natural and synthetic clay minerals permit colloidal particles to form upon hydration. These colloidal particles can exhibit repulsive electrical surface charges, which can then be able to maintain a uniform suspension in solution. With the addition of an ionic compound, such as, for example, USP sodium chloride, USP potassium chloride, to the colloidal suspension, the repulsive particle charges can be reduced significantly, allowing the formation of a viscous, aqueous gel with rheological characteristics that can be typical of the clay mineral used. The formed gel can demonstrate at least one property such as the flow properties and the rheological behavior classically termed thixotropic, wherein a semi-solid gel can be induced by shaking or stirring, to become a sol (a thin liquid) and revert once again to a semi-solid gel upon standing.

The at least one gelling agent can be present in the composition in any desired or effective amount. In some embodiments the at least one gelling agent is present in a concentration ranging from about 0.1 wt % to about 10 wt % of the entire composition. In some embodiments the at least one gelling agent is present in a concentration ranging from about 0.2 wt % to about 5 wt % of the entire composition. In some embodiments the at least one gelling agent is present in a concentration ranging from about 0.4 wt % to about 1.0 wt % of the total weight of the composition. In some embodiments the at least one gelling agent is present in a concentration ranging from about 0.5 wt % to about 0.8 wt % of the total weight of the composition. By varying the concentration of the at least one gelling agent, the gel composition can have consistencies that range from a heavy liquid to a thick, slightly cloudy gel.

In some embodiments, at least one organic modifier can be combined with the at least one gelling agent in order to realize the best properties of both. The at least one gelling agent and the at least one organic modifier can be used in a combination, such as an approximate ratio of about 4 parts of at least one gelling agent to about 1 part of at least one organic modifier. The at least one organic modifier can generally be cellulosic in nature, and can typically be used in the art to form thixotropic gels. Non-limiting examples of the at least one organic modifier include hydroxypropyl methyl cellulose, guar hydroxypropyl trimonium chloride, carbomer, xanthan gum, polyethylene glycol (PEG) block polymers, and polyvinylpyrrolidone.

In all embodiments of the topical dermatological formulations or dermatological cleansers of the present disclosure that are gel formulations, the gelling agent or agents are specifically chosen to impart certain desirable rheological characteristics to the gel formulation. In all embodiments of the topical dermatological formulations or dermatological cleansers of the present disclosure, the gelling agent utilized must impart these desirable rheological characteristics to the gel formulation at the desired target acidic pH required for the formulation to exhibit efficacy in acidifying the skin and treating the disease or disorder to be treated. Moreover, the choice of thickening agent, viscosity enhancing agent, or gelling agent used will generally be determined by what is most compatible with human skin, and what is least antigenic.

Preservative Agents

Optionally, and in some embodiments, the topical dermatological formulations or dermatological cleansers of the present disclosure can comprise a preservative agent. The selection of an appropriate preservative agent must be made carefully to assure that such topical dermatological formulations or dermatological cleansers do not cause irritation or sensitivity of the skin to which they are applied. Moreover, the preservative agent to be used in the topical dermatological formulations or dermatological cleansers of the present disclosure can comprise a preservative agent from the list of preservatives allowed in cosmetic products by member states of the European Union, which include benzoic acid and its salts, propionic acid and its salts; salicylic acid and its salts; hexa-2,4-dienoic acid and its salts; formaldehyde and para formaldehyde; biphenyl-2-ol and its salts; pyrithione zinc; inorganic sulfites and hydrogensulfites; chlorobutanol; 4-hydroxybenzoic acid and its salts and esters; 3-acetyl-6-methylpyran-2,4-(3H)-dione and its salts; formic acid and its sodium salt; 3,3'-dibromo-4,4'-hexamethylenedioxydibenzamidine and its salts; thiomersal; phenylmercuric salts; undec-10-enoic acid and its salts; 5-pyrimidinamine, 1,3-bis-(2-ethylhexyl)hexahydro-5-methyl; 5-bromo-5-nitro 1,3-dioxane; bronopol; 2,4-dichorobenzyl alchohol; 1-(4-cholophenyl)-3-(3,4-dichlorophenyl)urea; chlorocresol; 5-chloro-2-(2,4-dichlorophenoxy)phenol; chloroxylenol; N,N"-methylenebis [N'[3-(hydroxymethyl)-2,5-dioxoimidazolidin-4-yl]urea]; poly(methylene), α,ω-bis [[[(aminoiminomethyl)amino]iminomethyl]amino]-, dihydrochloride; 2-phenoxyethanol; methenamine; methenamine 3-chloroallylochloride; 1-(4-chlorophenoxy)-1-(imidazol-1-yl)-3,3-dimethylbutan-2-one; 1-(4-chlorophenoxy)-1-(imidazol-1-yl)-3,3-dimethylbutan-2-one; benzyl alcohol; 1-hydroxy-4-methyl-6-(2,4,4-trimethylpentyl)-2 pyridon and its monoethanolamine salt; 2,2'-methylenebis(6-bromo-4-chlorophenol); 4-isopropyl-m-cresol; mixture of 5-chloro-2-methyl-isothiazol-3(2H)-one and 2-methylisothiazol-3(2H)-one with magnesium chloride and magnesium nitrate; 2-benzyl-4-chlorophenol; 2-chloroacetamide; N,N'-bis(4-chlorophenyl)-3,12-diimino-2,4,11,13-tetraazatetradecanediamidine and its digluconate, diacetate and dihydrochloride; 1-phenoxypropan-2-ol; alkyl (C12-C22) trimethyl ammonium bromide and chloride; 4,4-dimethyl-1,3,-oxazolidine; N-(hydroxymethyl)-N-(dihydroxymethyl-1,3-dioxo-2,5-imidazolidinyl-4)-N'-(hydroxymethyl)urea; benzenecarboximidamide, 4,4'-(1,6-hexanediylbis(oxy))bis-, and its salts (including isothionate and p-hydroxybenzoate); glutaraldehyde (pentane-1,5-dial); 5-ethyl-3,7-dioxa-1-azabicyclo[3.3.0] octane; 3-(p-chlorophenoxy)-propane-1,2-diol; sodium hydroxymethylamino acetate; silver chloride deposited on titanium dioxide; benzenemethanaminium, N,N-dimethyl-N-[2-[2-[4-(1,1,3,3-tetramethylbutyl)phenoxy]ethoxy]ethyl]-, chloride; benzalkonium chloride, bromide an saccharinate; methanol, (phenylmethoxy)-; 3-iodo-2-propynylbutylcarbamate; and 2-methyl-2H-isothiazol-3-one. (See Annex V of the REGULATION (EC) No. 1223/2009 OF THE EUROPEAN PARLIAMENT AND OF THE COUNCIL of 30 Nov. 2009 on cosmetic products.)

Other example preservative agents to be used in the topical dermatological formulations or dermatological cleansers of the present disclosure can comprise methyl-parabens, ethyl-parabens, propyl-parabens, butyl-parabens, imidazolidinyl urea, diazolidinyl urea, methylchloro-isothiazolone, methyl-isothiazolone, iodopropynyl butylcarbamate, methyldibromo glutaronitrile, sodium benzoate, chloracetamide, phenoxyethanol, triclosan, DMDM-hydantoin, quatermium-15, benzylalcohol, caprylyl glycol, propylene glycol, iodopropynyl, paraben, caprylic acid, and potassium sorbate, or combinations thereof. In some embodiments, the topical dermatological formulations or dermatological cleansers of the present disclosure can contain a synergistic blend of 1,2-hexanediol and 1,2-octanediol (or caprylyl glycol), which is commercially available under the trade name of SymDiol®68 from Symrise Inc., of Teterboro, N.J.

Unlike the topical dermatological formulations or dermatological cleansers, the bath water conditioners of the present disclosure generally do not require additional preservative agents since they are prepared and delivered as dry powders which do not support microbial growth. Additionally, both the bath water conditioners and the topical dermatological formulations and dermatological cleansers of the present disclosure usually comprise a calcium chelation agent such as EDTA, which can also have antimicrobial activity, and therefore can also serve as a type of preservative agent, whether present in the dry powder of a bathwater conditioner or a hydrogel for topical application.

When present, the preservative agent, or combination of preservative agents, used in the topical formulations or dermatological cleansers used in concentrations of around 1 wt % or less. In some embodiments the preservative agent is present in a concentration ranging from about 0.01 wt % to about 8.0 wt %. In some embodiments the preservative agent is present in a concentration ranging from about 0.05 wt % to about 4.0 wt %. In some embodiments the preservative agent is present in a concentration ranging from about 0.1 wt % to about 2.0 wt %. In some embodiments the preservative agent is present in a concentration ranging from about 0.5 wt % to about 1.0 wt %.

Osmolality Adjusting Agents

In some embodiments, the topical dermatological formulations, dermatological cleansers or bathwater conditioners of the present disclosure comprise an osmolality adjusting agent, such as a mineral salt. In some embodiments the osmolality adjusting agent present in the topical dermatological formulations, dermatological cleansers or bathwater conditioners is selected from sodium chloride or potassium chloride, or combinations thereof. When present, the osmolality adjusting agent serves to approximately match the osmolality of the topical dermatological formulation or dermatological cleanser to approximately that of healthy human tissues, which ranges from about 285 to about 295 milliosmoles per kilogram, or approximately 0.9% w/v sodium chloride, or about 9.0 g sodium chloride per liter of aqueous formulation. In some embodiments, the topical dermatological formulations or dermatological cleanser of the present disclosure comprise an osmolality adjusting agent for improved feel of the formulation on the skin.

Additional Components

In some embodiments, the topical dermatological formulations or dermatological cleansers of the present disclosure comprise additional components that are selected from the conventional ingredients commonly included in cosmetic preparations. For example, the dermatological formulations of the present disclosure can comprise water, oils, stiffeners, emollients, emulsifying agents, humectants, hydrophilic or lipophilic active agents, antioxidants, fragrances, fillers, UV screening agents, and colorants. Stiffeners are usually oil-soluble fatty alcohols selected from stearyl alcohol, cetyl alcohol, lauryl alcohol and myristyl alcohol, or combinations thereof. Emollients are usually isopropyl myristate, lanolin, lanolin derivatives, isopropyl palmitate, isopropyl stearate and corresponding sebacates, and combinations thereof. Emulsifying agents are preferably non-ionic and are usually sorbitan monooleate and polyoxyl 40 stearate, or combinations thereof. Humectants are usually polypropylene glycol, sorbitol, glycerin or combinations thereof. Oils, when present, can include mineral oils, vegetable oils (i.e., Jojoba oil, apricot oil, and sesame oil), synthetic oils (i.e., myristyl myristate, octyl palpitate, hydrogenated polyisobutene), silicone oils (i.e., cyclomethicone) and fluorinated oils (i.e., perfluoropolyethers). Fatty alcohols, such as cetyl alcohol, and fatty acids may be added to these oils a well. Hydrophilic active agents which can also be incorporated into the topical dermatological compositions or dermatological cleansers of the present disclosure can include proteins or protein hydrolysates, amino acids, polyols, especially glycerol or sorbitol, urea, allantoin, sugars and sugar derivatives. Lipophilic active agents which can also be incorporated into the topical dermatological compositions or dermatological cleansers of the present disclosure can include retinol (vitamin A) and derivatives thereof, tocopherol (vitamin E) and derivatives thereof, essential fatty acids, ceramides, essential oils, and salicylic acid and derivatives thereof. UV screening agents with lipophilic or hydrophilic properties can also be included in the compositions of the present disclosure, either alone, or in combination with oxides of titanium and of zinc.

All of these additional components, or various combinations thereof, can be present in concentrations of around 1 wt % or less. In some embodiments the additional components can be present in a concentration ranging from about 0.01 wt % to about 1.0 wt %. In some embodiments the additional components can be present in a concentration ranging from about 0.02 wt % to about 0.5 wt %. In some embodiments the additional components can be present in a concentration ranging from about 0.04 wt % to about 0.25 wt %. In some embodiments the additional components can be present in a concentration ranging from about 0.05 wt % to about 0.1 wt %.

Types of Formulations

Topical Dermatological Formulations

The topical dermatological formulations of the present disclosure can be provided in any form suitable for the immediate application to the skin—whether locally to a particular affected area, or more generally. The formulations may be in the form of a liquid, gel, lotion, crème, ointment or aerosol. Ideally, the formulations are formulated as a gel or lotion to provide for longer lasting coverage to a particular affected area of the skin. Such gels or lotions may be water based, and will contain a suitable gelling or thickening agent. Alternatively, the formulation may be provided as an emulsion, either an oil-in-water emulsion of a water-in-oil emulsion. Such emulsions typically are prepared using conventional ingredients known to be compatible with the skin, and suitable for direct application to the skin, as outlined above.

As noted, the topical dermatological formulations of the present disclosure can be in the form of a liquid, gel, lotion, crème, ointment or aerosol. As such, the topical dermatological formulations are designed to be applied directly to affected skin. One method of application would simply be to rub the formulation into the affected skin. Alternative, if formulated as an aerosol, the formulation can be applied by simply spraying aerosol onto the affected skin. This method of application has the advantage of not physically disturbing the skin, which may be advantageous when the skin is highly inflamed, tender and/or sensitive to the touch.

Bathwater Conditioners

The present disclosure also provides for bathwater conditioners that can be used for treatment of large areas of the skin while bathing. In these embodiments, an amount of the powdered bathwater conditioner is added to the bath while the bath is being drawn or immediately thereafter, and is mixed well with the bathwater. Once thoroughly mixed the patient need only soak the affected areas, or indeed the entire body, in the conditioned bathwater for a period of time. In some embodiments, the bathwater conditioner after being mixed with the bath is sufficient to allow for treatment by soaking the affected skin, or the entire body, for a period of 5 min, 10 min, 15 min, 20 min, 30 min, 40 min, 50 min or 60 min. Following the treatment by soaking, the patient may choose to rinse off the conditioned bathwater with fresh water, or may simply towel dry and dress without rinsing. Care should be taken to avoid introducing conditioned bathwater into the eyes, since it will be mildly acidic.

Dermatological Cleansing Compositions—Body Washes and Bar Soaps

In addition to the dermatological compositions and bathwater conditioners described herein, the present disclosure also provides for dermatological cleansing compositions that incorporate many of the same features and components as the disclosed dermatological compositions and bathwater conditioners. In some embodiments these dermatological cleansing compositions are liquid body washes. In other embodiments these dermatological cleansing compositions are bar "soaps." In both of these embodiments of dermatological cleansing compositions, the included components are carefully chosen to achieve an appropriately-acidic and/or calcium chelating composition. In some embodiments the dermatological cleansing compositions comprise an acidifying agent, a calcium chelating agent, and some type or combination of types of synthetic detergents.

In some embodiments the synthetic detergent or detergents used the dermatological cleansing compositions of the present disclosure is at least one form of cationic detergent, at least one form of ampholytic (or amphoteric) detergent, or some combination thereof. The cationic detergents used in these embodiments generally contain a long-chain cation, usually comprising at least one quaternary amine group that is responsible for imparting the positive charge and surface-active properties of the molecule. Often provided in a powder form, a paste, or as an aqueous solution as a component for compounding, such synthetic cationic detergents can provide wetting, foaming and emulsifying properties, and in some instances, germicidal properties. The ampholytic detergents used in these embodiments generally contain long-chain zwitterions (i.e., combinations of ionic groups having either a positive or a negative charge). In some embodiments, neutral or non-ionic detergents can also be used in combination with cationic and/or ampholytic detergents. Anionic detergents can also be used in the embodied dermatological cleansing compositions, however when such anionic detergents are used, they must be capable of providing wetting, foaming or emulsifying properties in the context of a final composition having a pH ranging from about pH 4.0 to about pH 6.0, and comprising one or more of the acidifying agents, as disclosed above.

Examples of cationic synthetic detergents (surfactants) that can be used in the dermatological cleansing compositions disclosed include octenidine dihydrochloride, cetyl trimethylammonium bromide, hexadecyl trimethyl ammonium bromide, cetyl trimethylammonium chloride, cetylpyridinium chloride, benzalkonium chloride, benzethonium chloride, 5-bromo-5-nitro-1,3-dioxane, dimethyldioctadecylammonium chloride, cetrimonium bromide, and dioctadecyldimethylammonium bromide. Examples of amphylitic (amphoteric) detergents (surfactants) that can be used in the dermatological cleansing compositions disclosed include 3-[(3-cholamidopropyl)dimethylammonio]-1-propanesulfonate, sultaines, such as cocamidopropyl hydroxysultaine, betataines, such as cocamidopropyl betaine, and lecitins. Examples of nonionic detergents (surfactants) that can be used in the dermatological cleansing compositions disclosed include the fatty alcohols, such as cetyl alcohol, stearyl alcohol, cetostearyl alcohol (a mixture of cetyl alcohol and stearyl alcohol), oleyl alcohol; polyoxyethylene glycol alkyl ethers, such as octaethylene glycol monododecyl ether, pentaethylene glycol monododecyl ether and Brij; polyoxypropylene glycol alkyl ethers; glucoside alkyl ethers, such as decyl glucoside, lauryl glucoside and octyl glucoside; polyoxyethylene glycol octylphenol ethers, such as Triton X-100; polyoxyethylene glycol alkylphenol ethers, such as Nonoxynol-9; Glycerol alkyl esters, such as glyceryl laurate, polyoxyethylene glycol sorbitan alkyl esters, such as sorbate; sorbitan alkyl esters; cocamide MEA; cocamide DEA; dodecyldimethylamine oxide; block copolymers of polyethylene glycol and polypropylene glycol; and polyethoxylated tallow amine. Examples of synthetic anionic detergents that can be used in these dermatological cleansing compositions include, for example, sodium cocyl isethionate, sodium lauroyl isethionate, sodium palmitate, sodium palmitate, sodium laureth sulfate, ammonium laureth sulfate, sodium myreth sulfate, ammonium lauryl sulfate, sodium laurel sulfate; and the docusates, dioctyl sodium sulfosuccinate, perfluorooctanesulfonate, perfluorobutanesulfonate, and linear alkylbenzene sulfonate.

In some embodiments the disclosed dermatological cleansing compositions contain additional ingredients designed to retain moisture in the epidermis following cleansing of the skin in a bath or shower. Such ingredients can include dermatologically acceptable humectants, including such compounds as propylene glycol, hexylene glycol, butylene glycol, glyceryl triacetate, vinyl alcohol, neoagarobiose, sugar alcohols and sugar polyols, such as glycerine and glycerol, sorbitol, xylitol and maltitol, polymeric polyols such as polydexrose, quillaia, urea, aloe vera gel, MP diol and alphahydroxy acids.

Additional ingredients can be included in the disclosed dermatological cleansing compositions. Besides humectants, such additional ingredients can include preservative agents, water, oils, stiffeners, emollients, emulsifying agents, hydrophilic or lipophilic active agents, antioxidants, fragrances, fillers, UV screening agents, and colorants, as described above.

Packaging

The disclosed compositions and formulations may be packaged to provide a single dose or multiple doses, and to provide a convenient means of transport, handling, and administration. The disclosed compositions and formulations may also be packaged in such a way as to protect the formulation from oxidation, bacterial contamination, or other forms of deterioration or degradation. For example, the disclosed compositions and formulations can be packaged into crimped tubes, airless containers, or sealed foil-lined packets, which may optimally contain enough of the composition or formulation for a single application, or a limited number of applications. The disclosed topical dermatological formulations and cleansing compositions can be packaged in larger containers designed for multiple applications. When packaged in such larger containers, those containers may be equipped with hand operated pumps or other mechanisms designed to facilitate the delivery of an appropriate volume of the composition or formulation, while reducing the likelihood of contamination or oxidation.

The disclosed bathwater conditioner formulations can be provided as dry powders in large, screw-top containers which may also contain a scoop or other measuring device that can be used to remove and transfer a uniform amount of the formulation. For example, the measuring device or scoop could be large enough to transfer a sufficient amount of the bathwater conditioner to condition the water of an average sized bath, so that to prepare a therapeutic bath the patient need only transfer one scoop of material to the bath and dissolve it completely in the bathwater before soaking in it.

Diseases and Disorders to be Treated

The disclosed topical dermatological formulations, dermatological cleansing compositions and bathwater conditioners are intended to treat diseases or disorders or conditions of the skin and mucous membranes which result from, result in, or are characterized by, an elevated epidermal pH (i.e., a pH greater than about 6.0), and/or which are associated with disruptions or dysfunctions of the epidermal barrier. The disclosed compositions and formulations are intended to treat diseases or disorders or conditions of the skin and mucous membranes which result from, result in, or are characterized by, alterations in the normal microbiome, such as by infection, invasion or overgrowth by pathogenic microorganisms. The disclosed compositions and formulations are intended to treat diseases or disorders or conditions of the skin and mucous membranes which result from, result in, or are characterized by, alterations in the normal microbiome, such as by infection, invasion or overgrowth by *Candida* spp., *Staphylococcus* spp., *Corynebacterium* spp., *Propionibacterium* spp., etc. The disclosed compositions and formulations may also be used prophylactically, in order to prevent, lessen, or delay the onset of the symptoms of a disease, disorder, or condition before it fully develops, by lowering the pH of the skin to within the desired range of from about 4.0 to about 6.0.

As such, the disclosed compositions and formulations may be used for treating, lessening the symptoms of, preventing the symptoms, or delaying the onset of symptoms of any of the following diseases, disorders, or conditions:

a) atopic dermatitis (which is known to be exacerbated by *S. aureus*—which colonizes the folds of the skin);
b) intertrigo (and other mucocutaneous infections attributed to *Candida* spp.);
c) webspace infections;
d) pitted keratolysis;
e) foul-smelling feet and axillae (often associated with overgrowth of *Corynebacterium* spp.);
f) erythrasma;
g) some forms of tinea corporis (when in the folds of the skin);
h) tinea pedis;
i) ichthyosis;
j) psoriasis;
k) acne;
l) rosacea;
m) seborrhoeic dermatitis;
n) diaper dermatitis;
o) some forms of irritant contact dermatitis;
p) keratosis pilaris;
q) xerosis; and
r) dermatological disorders commonly found among uremics.

Methods of Treatment

The methods of treatment to be employed with the disclosed dermatological compositions, dermatological formulations, dermatological cleansers, and bathwater conditioners will vary depending upon the disease, disorder, or condition to be treated, and its severity. The methods will also vary depending upon the nature of the subject to be treated; their species, gender, and age, etc. Optimal methods of treatment, including the choice of specific compositions, formulations, cleansers and conditioners, the form of those compositions, formulations, cleansers and conditioners, the frequency of administration, and the duration of treatment will be adjusted according to the response of the patient, and the efficacy of the treatment, as will be judged by the patient themselves, or by a health care provider who is directing the treatment. Specific details regarding the methods of treatment can be defined by a health care provider overseeing the treatment, or by the patient, as results are obtained.

Effective results will, in most cases, be achieved by topical application of a disclosed formulation in a thin layer directly over the affected area or areas, or in the area where one seeks to obtain a desired result, such as the folds of skin exhibiting Candidal intertrigo. In some embodiments, a disclosed formulation is topically administered after the skin has been first cleansed with a disclosed dermatological cleansing composition as disclosed herein. In some embodiments, such as when large areas of the skin are to be treated, it may be desirable to have the patient soak or take a bath in bathwater containing the bathwater conditioners as disclosed herein. In some embodiments, treatment may consist of topical application of thin layers of particular disclosed formulations followed by topical application of other prescription formulations designed to restore a disrupted epidermal barrier. In other embodiments, treatment may consist of topical application of thin layers of particular disclosed formulations in a particular order, interspersed with over-the-counter formulations, such as 1% hydrocortisone cream. In other embodiments, treatment may consist of topical application of thin layers of a particular disclosed formulation following treatment of the same area with sodium hypochlorite, such as treatment with a sodium hypochlorite gel as disclosed in U.S. Pat. No. 7,622,434. Alternatively, in still other embodiments, treatment may consist of having the patient first take a sodium hypochlorite bath as directed by their physician, followed by either having the patient soak or take a bath in bathwater containing the bathwater conditioners as disclosed herein, or applying the topical dermatological formulations disclosed herein to only the affected areas. In still other embodiments, treatment may consist of having the patient first take a sodium hypochlorite bath as directed by their physician, followed by either having the patient either soak or take a bath in bathwater containing the bathwater conditioners as disclosed herein, or wash with a dermatological cleanser as disclosed herein, before applying a topical dermatological formulations as disclosed herein to only the affected areas of the skin.

In some embodiments, treatment may consist of applying the topical dermatological formulations of the present disclosure to sterile gauze bandages or wound dressings, or saturating sterile gauze bandages or wound dressings with the disclosed formulations followed by prolonged topical application of the moistened or saturated gauze bandages or wound dressings as a compress. In such embodiments, the compress can be held in place over affected skin by any effective means, for a sufficient time to provide a desired effect.

Depending upon the disease, disorder, or condition to be treated, and its severity, and whether the treatment is being done for therapeutic or prophylactic reasons, effective results may be obtained with application rates of from one application every week, to once every day, to multiple applications per day. In some embodiments the topical dermatological formulations of the present disclosure are applied twice a day, with a first application at the start of a patient's day, following a bath or shower, and the second application at the end of the day, immediately prior to the patient retiring for sleep. Traditionally, such applications would occur in the morning and evening, but the time of application can be adjusted to the patient's daily schedule or routine.

In all embodiments, the duration of the treatment regimen can be adjusted according to the patient's needs and according to the response of the patient's disease or disorder to the treatment. Treatment can either be discontinued, or its frequency lessened, once symptoms diminish or disappear. Alternatively, it may be advantageous for treatments to continue for a fixed period beyond the diminution or disappearance of symptoms, and in other cases, it may be advantageous for treatment to continue indefinitely as a prophylactic treatment in patients who suffer from chronic elevation of the epidermal pH.

Kits

The embodiments of the present disclosure may be formulated, packaged and provided in a kit format, comprising one or more of the topical dermatological formulations, dermatological cleansers, and bathwater conditioners of the present disclosure, along with instructions for their use. Such kits may optionally include a means for estimating or measuring the pH of skin before and after treatment with one or more components of the kit. If a means for estimating or measuring the pH of skin before and after treatment is included, it can further require the inclusion of pH testing reagents, indicator (litmus) papers, or a non-invasive, electronic pH meter. The kit may include other dermatological formulations to be administered to the skin either before or after treatment with a topical dermatological formulation, a dermatological cleanser, or a bathwater conditioner of the present disclosure. Ideally, the kit will include instructions for the use of any and all components of the kit. The kit may be conveniently packaged, with labeled containers containing the different components of the kit.

It is also within the purview of the present disclosure to include within said kit, additional materials that assist in treating the skin by bathing in bathwater conditioned with a bathwater conditioner of the present disclosure, and/or cleansing the skin with a dermatological cleanser of the present disclosure, and/or applying a topical dermatological formulation of the present disclosure. Examples of such materials might include spray bottles, measuring devices, specialty applicators, dressings and bandages, and other compositions that are specifically formulated to maintain, or otherwise not deleteriously alter, desired skin acidity and an appropriate epidermal calcium gradient.

EXAMPLES

Exemplary Formulations

Exemplary Formulation A—Bathwater Conditioner

Provided herewith is a first exemplary formulation that is a bathwater conditioner according to the disclosed formulations provided herein.

| Component | Function | Weight % |
| --- | --- | --- |
| Glucono-delta-lactone | acidification agent | 0.01-1.0 |
| Apple Cider Vinegar Powder IP | acidification agent | 84-95 |
| disodium EDTA | calcium chelation agent | 5.0-15.0 |
| | | 100.00 |

Exemplary Formulation B—Topical Dermatological Gel

Provided herewith is a first exemplary formulation that is a topical dermatological gel according to the disclosed formulations provided herein.

| Component | Function | Weight % |
| --- | --- | --- |
| Distilled water | solvent/carrier | q.s. |
| Glucono-delta-lactone | acidification agent | 0.05-5.0 |
| Apple Cider Vinegar Powder IP | acidification agent | 0.01-1.0 |
| Disodium EDTA | calcium chelation agent | 0.01-0.10 |
| 1,2-hexanediol:1,2-octanediol | preservative | 0.01-1.0 |
| Xanthan gum | gelling agent | 0.1-1.0 |
| | | 100.00 | pH 5.0-5.5

Exemplary Formulation C—Topical Dermatological Gel

Provided herewith is a first exemplary formulation that is a topical dermatological gel according to the disclosed formulations provided herein.

| Component | Function | Weight % |
| --- | --- | --- |
| Distilled water | solvent/carrier | q.s. |
| Glucono-delta-lactone | acidification agent | 0.001-0.10 |
| Apple Cider Vinegar Powder IP | acidification agent | 0.05-5.0 |
| Disodium EDTA | calcium chelation agent | 0.01-0.10 |
| 1,2-hexanediol:1,2-octanediol | preservative | 0.01-1.0 |
| Xanthan gum | gelling agent | 0.1-1.0 |
| | | 100.00 | pH 4.8-5.3

What is claimed is:

1. A method of treating a dermatological disease or disorder at least partially characterized by an abnormally high skin pH, comprising administering a therapeutically effective amount of a topical dermatological formulation with a pH between 4.2 and 4.8 to the affected skin of a patient, wherein the dermatological formulation comprises:
  vinegar powder,
  glucono delta-lactone,
  an EDTA calcium chelation agent,
  a preservative, and
  a gelling agent; and
wherein the disease or disorder is selected from:
  a) atopic dermatitis;
  b) intertrigo;
  c) webspace infections;
  d) pitted keratolysis;
  e) foul-smelling feet and axillae;
  f) erythrasma;
  g) ichthyosis;
  h) psoriasis;
  i) acne;
  j) rosacea;
  k) seborrhoeic dermatitis;
  l) diaper dermatitis;
  m) irritant contact dermatitis;
  n) keratosis pilaris; and
  o) xerosis.

2. A method of treating a dermatological disease or disorder at least partially characterized by an abnormally high skin pH, comprising cleansing the affected skin of a patient with a therapeutically effective amount of a dermatological cleanser having a pH between 4.2 and 4.8 comprising:
  vinegar powder,
  glucono delta-lactone,
  at least one calcium complexing agent, and
  at least one synthetic detergent; and,
wherein the disease or disorder is selected from:
  a) atopic dermatitis;
  b) intertrigo;
  c) webspace infections;
  d) pitted keratolysis;
  e) foul-smelling feet and axillae;
  f) erythrasma;
  g) ichthyosis;
  h) psoriasis;
  i) acne;
  j) rosacea;
  k) seborrhoeic dermatitis;
  l) diaper dermatitis;
  m) irritant contact dermatitis;
  n) keratosis pilaris; and
  o) xerosis.

3. The method of claim 2, wherein the dermatological cleanser further comprises one or more of an osmolality adjusting agent, an oil, a stiffener, an emollient, an emulsifying agent, a humectant, a hydrophilic or lipophilic active agent, an antioxidant, a fragrance, a filler, a UV screening agent, and a colorant.

4. A method of treating a dermatological disease or disorder at least partially characterized by an abnormally high skin pH, comprising dissolving or diluting a therapeutically effective amount of a powdered bathwater conditioner in bathwater to make conditioned bathwater, wherein the conditioned bathwater is made to have a pH between 4.2 and 4.8 after the addition of the powdered bathwater conditioner, and having a patient with the dermatological disease or disorder soak themselves in the conditioned bathwater, wherein the bathwater conditioner comprises therapeutically effective amounts of the following:
  vinegar powder in a concentration between 84 wt % and 95 wt % of a total weight of the powdered bathwater conditioner,
  glucono delta-lactone, and
  at least one calcium complexing agent; and
wherein the disease or disorder is selected from:
  a) atopic dermatitis;
  b) intertrigo;
  c) webspace infections;
  d) pitted keratolysis;
  e) foul-smelling feet and axillae;
  f) erythrasma;
  g) ichthyosis;
  h) psoriasis;
  i) acne;
  j) rosacea;
  k) seborrhoeic dermatitis;
  l) diaper dermatitis;
  m) irritant contact dermatitis;
  n) keratosis pilaris; and
  o) xerosis.

5. The method of claim 3, wherein the vinegar powder comprises apple cider vinegar powder.

6. The method of claim 4, wherein the calcium complexing agent is one or both of the following: EDTA and EGTA.

7. The method of claim 4, wherein the cleanser further comprises at least one preservative agent.

8. The method of claim 7, wherein the preservative agent is a blend of 1,2-hexanediol and 1,2-octanediol.

* * * * *